US00PP19387P2

(12) United States Plant Patent
Kleinhanns

(10) Patent No.: US PP19,387 P2
(45) Date of Patent: Oct. 28, 2008

(54) *VERBENA* PLANT NAMED 'VEGAS BRIGHT PINK'

(50) Latin Name: *Verbena hybrida*
Varietal Denomination: Vegas Bright Pink

(75) Inventor: Christoph E. Kleinhanns, Gernrode (DE)

(73) Assignee: Hamer Bioemzaden B.V., H.I. Ambacht (NL)

( * ) Notice: Subject to any disclaimer, the term of this patent is extended or adjusted under 35 U.S.C. 154(b) by 0 days.

(21) Appl. No.: 11/827,391

(22) Filed: Jul. 11, 2007

(51) Int. Cl.
*A01H 5/00* (2006.01)

(52) U.S. Cl. ..... Plt./308

(58) Field of Classification Search ..... Plt./308
See application file for complete search history.

*Primary Examiner*—Wendy C. Haas
(74) *Attorney, Agent, or Firm*—Jondle & Associates, P.C.

(57) ABSTRACT

A *Verbena* cultivar particularly distinguished by large, bright pink flowers, good branching and garden performance and tolerance to mildew is disclosed.

1 Drawing Sheet

Genus and species: *Verbena hybrida.*
Variety denomination: 'Vegas Bright Pink'.

BACKGROUND OF THE NEW PLANT

The present invention comprises a new and distinct cultivar of *verbena,* botanically known as *Verbena hybrida,* and hereinafter referred to by the cultivar name 'Vegas Bright Pink'. 'Vegas Bright Pink' originated from a polycross breeding system in June 2003 in Quedlinburg, Germany. The female parent was a *verbena* plant with light pink flowers while the male parent was a *verbena* plant with pink flowers.

The new cultivar was first propagated in summer of 2006 from mother stock and has been asexually reproduced through vegetative cuttings for four generations. The present invention has been found to retain its distinctive characteristics.

SUMMARY OF THE INVENTION

The following are the most outstanding and distinguishing characteristics of this new cultivar when grown under normal horticultural practices in Quedlinburg, Germany.

1. Large bright pink flowers;
2. Strong branching growth;
3. Good garden performance; and
4. Tolerance to mildew.

DESCRIPTION OF THE PHOTOGRAPH

This new *Verbena* plant is illustrated by the accompanying photograph which shows the overall plant habit, including blooms, buds and foliage of the plant in full color, the colors shown being as true as can be reasonably obtained by conventional photographic procedures.

DESCRIPTION OF THE NEW CULTIVAR

The following detailed descriptions set forth the distinctive characteristics of 'Vegas Bright Pink'. The data which define these characteristics were collected from asexual reproductions carried out in Quedlinburg, Sachsen-Anhalt, Germany. Data was collected on plants in 12-liter pots in October. Color references are primarily to the R.H.S. Colour Chart of The Royal Horticultural Society of London (R.H.S.) ($4^{th}$ ed).

DETAILED BOTANICAL DESCRIPTION

Classification:
- *Family.*—Verbenaceae.
- *Botanical.*—*Verbena hybrida.*
- *Common name.*—*Verbena.*

Parentage:
- *Female parent.*—*Verbena* with light pink flowers.
- *Male parent.*—*Verbena* with different pink colors.

Plant:
- *Form.*—Trailing.
- *Growth and branching habit.*—Trailing, basal.
- *Height.*—20.0 cm to 40.0 cm.
- *Width.*—Radius: 30.0 cm to 40.0 cm. Diameter: 60.0 cm to 80.0 cm.
- *Time to produce a finished flowering plant.*—10 to 14 weeks.
- *Time to initiate and develop roots.*—4 to 5 weeks.
- *Root description.*—Fine rooting system, with white to light brown roots.

Stems:
- *Number of branches per plant.*—80 to 100.
- *Length.*—25.0 cm to 70.0 cm.
- *Diameter.*—Radius: 0.1 cm to 0.2 cm. Diameter: 0.2 cm to 0.4 cm.
- *Internode length.*—3.0 cm to 8.0 cm.
- *Color.*—RHS 143D (Light green).
- *Anthocyanin.*—Absent.
- *Texture.*—Rough with small hairs.

Leaves:
- *Arrangement.*—Opposite.
- *Immature leaf.*—General color: RHS 135B (Light green). Upper surface: RHS 143C (Light green). Lower surface: RHS 143D (Lighter green).
- *Mature leaf.*—General color: RHS 137A (Dark green). Upper surface: RHS 143A (Dark green). Lower surface: RHS 143B (Lighter green). Length: 4.0 cm to 6.0 cm. Width: 2.0 cm to 4.0 cm.

*Shape.*—Oval.
*Apex.*—Differs from round to spiky.
*Base.*—Round running to the short petiole.
*Margin.*—Double ridged.
*Texture.*—Rough, pubescent.
*Venation.*—Distinct on the upper surface, very distinct on the lower surface.
*Venation color.*—RHS 143D (Softer green than the leaf).
*Petioles.*—Length: 0.2 cm to 0.7 cm. Diameter in cm: Radius: 0.1 cm to 0.2 cm. Diameter: 0.2 cm to 0.4 cm. Color: RHS 143C (Light green). Texture: Winged from the leaf, some hairs.

Flower buds:
*Shape.*—Nearly covered in pubescent sepals.
*Length.*—0.5 cm to 2.0 cm.
*Diameter.*—Radius: 0.2 cm to 0.3 cm. Diameter: 0.4 cm to 0.6 cm.
*Color* (*at tight bud*).—RHS 68A (Pink).

Inflorescence:
*Blooming habit* (*flowering season*).—May to November.
*Lastingness of individual blooms on the plant.*—About 7 days, but very much dependent on irrigation, fertilizer and temperature.
*Fragrance.*—Soft.
*Inflorescence type.*—Ear type.
*Length of inflorescence.*—2.0 cm to 4.0 cm.
*Diameter of inflorescence in cm.*—Radius: 3.0 cm to 4.0 cm. Diameter: 6.0 cm to 8.0 cm.
*Number of florets per inflorescence.*—15 to 30. Peduncle: None.

Florets:
*Floret form.*—5 petals, flat flower with long tube.
*Floret length.*—2.0 cm to 3.5 cm.
*Floret diameter.*—Radius: 1.0 cm to 1.5 cm. Diameter: 2.0 cm to 3.0 cm.
*Immature flower.*—General color: RHS 61C (Dark Pink). Upper surface: RHS 68A (Dark pink, lighter than RHS 61C). Lower surface: RHS 68B (Light pink).
*Mature flower.*—General color: RHS 68B (Pink) to RHS 68D (Rose). Upper surface: RHS 68B (Pink). Lower surface: RHS 68D (Rose).
*Corolla tube length.*—2.0 cm to 3.0 cm.
*Corolla tube color.*—RHS 145D (Light green).

Petals:
*Length of lobe.*—2.0 cm to 4.0 cm.
*Diameter of lobe.*—Radius: 0.3 cm to 0.5 cm. Diameter: 0.6 cm to 1.0 cm.
*Lobe shape.*—Soft waved.
*Apex.*—Split.
*Base.*—Fused.
*Margin.*—Soft waved.

Calyx:
*Arrangement.*—Tube shaped.
*Sepals.*—Shape: Fused. Length: 0.5 cm to 1.5 cm. Diameter: Radius: 0.1 cm to 0.2 cm. Diameter: 0.3 cm to 0.4 cm. Color: RHS 145A (Soft green with lighter stripes of green). Apex: Spiky. Base: Round. Margin: Fused. Texture: Soft, pubescent.

Reproductive organs:
*Stamens.*—Quantity: 5. Shape: with a short stem. Color: RHS 149D (Light yellow-green). Filament length: 0.1 cm to 0.2 cm. Filament diameter: Radius: Less than 0.1 cm. Diameter: Less than 0.1 cm.
*Anther.*—Shape: Oval. Color: RHS 149D (Light yellow-green). Length: 0.1 cm to 0.2 cm. Diameter: Radius: Less than 0.1 cm. Diameter: 0.1 cm.
*Pollen.*—Color: RHS 149D (Light yellow-green). Amount: Moderate.
*Pistils.*—Number: 1. Length: 1.5 cm to 2.0 cm. Diameter: Radius: Less than 0.1 cm. Diameter: Less than 0.1 cm.
*Stigma.*—Color: RHS 145A (Green). Shape: Round to oval. Length: 0.1 cm. Diameter: Radius: Less than 0.1 cm. Diameter: Less than 0.1 cm.
*Style.*—Color: RHS 145A (Green). Length: 1.4 cm to 1.9 cm. Diameter: Radius: Less than 0.1 cm. Diameter: Less than 0.1 cm. Shape: running wider as getting nearer to the stigma.

Seeds:
*Color.*—RHS 152A (Greenish-brown).
*Length.*—0.3 cm to 0.8 cm.
*Diameter.*—Radius: Less than 0.1 cm to 0.1 cm. Diameter: 0.1 cm to 0.2 cm. Shape: Rough, longish.

Disease and insect resistance: Tolerant to mildew.

COMPARISON WITH KNOWN CULTIVARS

'Vegas Bright Pink' differs from the female parent *Verbena* plant in that the female parent has a more upright growth habit than 'Vegas Bright Pink'. Additionally, 'Vegas Bright Pink' has a pink flower color, while the female parent has a light pink flower color.

'Vegas Bright Pink' differs from the male parent *Verbena* plant in that 'Vegas Bright Pink' has larger flowers and a more branching plant habit than the male parent.

'Vegas Bright Pink' differs from the commercial *Verbena* variety 'Temari Patio Coral Pink' (unpatented) in that 'Temari Patio Coral Pink' has less of a trailing growth habit than 'Vegas Bright Pink'.

I claim:

1. A new and distinct cultivar of *Verbena* plant as described and shown herein.

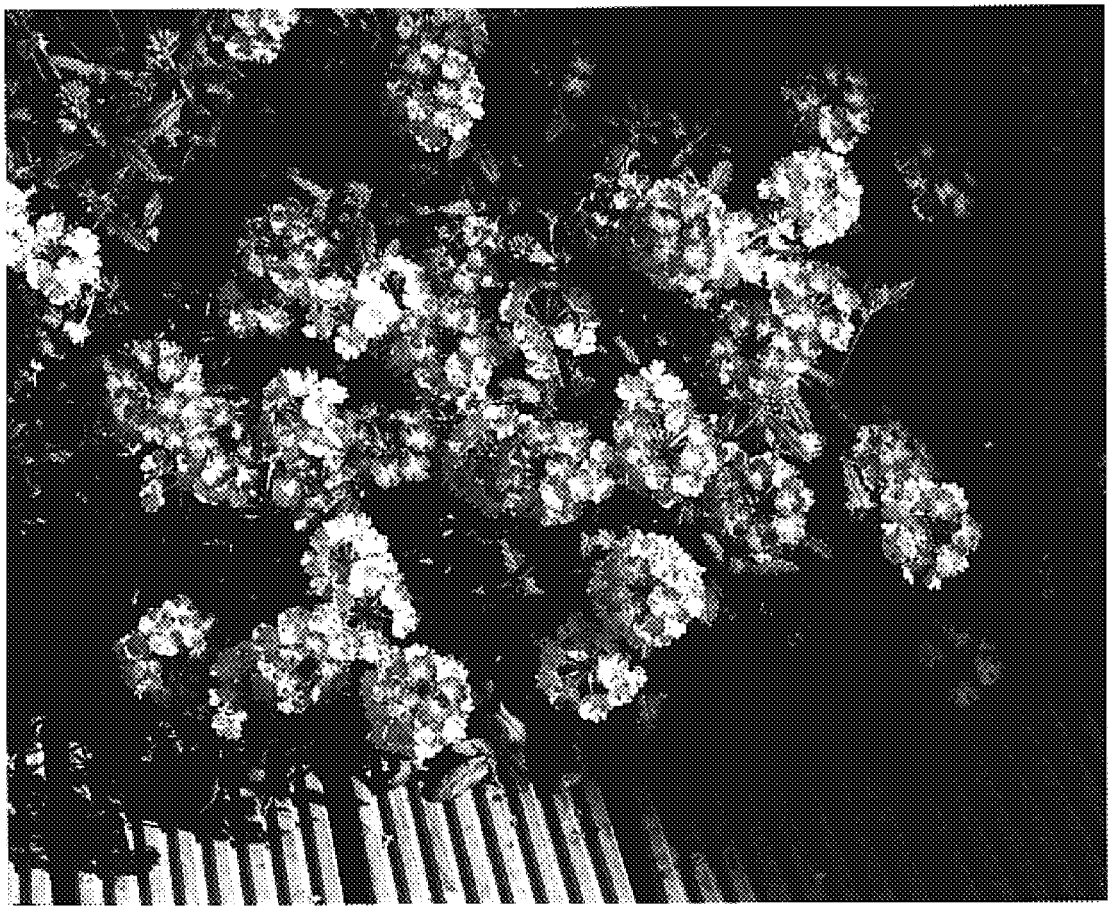

* * * * *